US012179821B2

(12) United States Patent
Cho et al.

(10) Patent No.: US 12,179,821 B2
(45) Date of Patent: Dec. 31, 2024

(54) FOLDING CART FOR LOADING IN VEHICLE

(71) Applicants: Hyundai Motor Company, Seoul (KR); Kia Corporation, Seoul (KR); SEGOS, Incheon (KR); KBI DONGKOOK IND. CO., LTD., Seoul (KR)

(72) Inventors: Min Ho Cho, Gyeonggi-do (KR); Sung Joon Kang, Incheon (KR); In Chan Jeong, Ulsan (KR)

(73) Assignees: Hyundai Motor Company, Seoul (KR); Kia Corporation, Seoul (KR); SEGOS, Incheon (KR); KBI Dongkook Ind. Co., Ltd., Seoul (KR)

( * ) Notice: Subject to any disclaimer, the term of this patent is extended or adjusted under 35 U.S.C. 154(b) by 313 days.

(21) Appl. No.: 17/732,875

(22) Filed: Apr. 29, 2022

(65) Prior Publication Data
US 2023/0060451 A1    Mar. 2, 2023

(30) Foreign Application Priority Data

Aug. 26, 2021    (KR) .......................... 10-2021-0113464

(51) Int. Cl.
*B62B 3/04*    (2006.01)
*A61L 2/10*    (2006.01)
*B62B 3/02*    (2006.01)

(52) U.S. Cl.
CPC    *B62B 3/04* (2013.01); *A61L 2/10* (2013.01); *B62B 3/027* (2013.01)

(58) Field of Classification Search
CPC .................................. B62B 3/04; B62B 3/027
See application file for complete search history.

(56) References Cited

U.S. PATENT DOCUMENTS

| 8,979,115 | B1 * | 3/2015 | Baron | B62B 3/106 |
| | | | | 280/DIG. 4 |
| 10,640,135 | B1 * | 5/2020 | Geffen | B62B 3/02 |
| 10,875,561 | B1 * | 12/2020 | Marker | B62B 3/04 |
| 2006/0076743 | A1 * | 4/2006 | Dunser | B62B 5/069 |
| | | | | 280/33.992 |
| 2010/0230934 | A1 * | 9/2010 | Fine | B62B 3/027 |
| | | | | 280/651 |

(Continued)

FOREIGN PATENT DOCUMENTS

KR    20140120515 A    10/2014

*Primary Examiner* — Erez Gurari
(74) *Attorney, Agent, or Firm* — Fox Rothschild LLP

(57) ABSTRACT

The present invention relates to a folding cart for loading in a vehicle, including a cart body configured to load the goods, the leg capable of the height adjustment and the folding and unfolding operations by the rotation, and the handle with sterilizing and disinfecting functions of the goods in the cart body. The cart body may be loaded with the goods (luggage) in the luggage room or the trunk of the vehicle by the user's simple operation, thereby further facilitating the loading work of the purchased goods in the vehicle, and the movement of the cart body loaded in the vehicle may be controlled, thereby preventing breakage or damage to the goods. Further, UV LED may be provided on the handle in the state where the cart body is loaded in the vehicle to sterilize and disinfect the goods in the cart body.

14 Claims, 17 Drawing Sheets

(56) References Cited

U.S. PATENT DOCUMENTS

| | | | | |
|---|---|---|---|---|
| 2010/0237753 A1* | 9/2010 | Reynolds | ............... | A47K 10/32 |
| | | | | 312/45 |
| 2011/0109056 A1* | 5/2011 | Hutchinson | ............... | B62B 3/04 |
| | | | | 280/79.2 |
| 2011/0182769 A1* | 7/2011 | Rich | ......................... | A61L 2/18 |
| | | | | 422/292 |
| 2012/0067474 A1* | 3/2012 | Fellema | ............... | B62B 3/1448 |
| | | | | 150/154 |
| 2012/0193894 A1* | 8/2012 | Fine | ..................... | B62B 5/0003 |
| | | | | 280/651 |
| 2014/0346757 A1* | 11/2014 | Fine | ......................... | B62B 3/027 |
| | | | | 280/651 |
| 2019/0167826 A1* | 6/2019 | Winslow | ............... | A61N 5/0624 |
| 2020/0223465 A1* | 7/2020 | Geffen | ..................... | B62B 3/027 |
| 2020/0239054 A1* | 7/2020 | Darvish | ............... | B62B 3/027 |
| 2022/0032984 A1* | 2/2022 | O'Donnell | ............ | B62B 5/0003 |
| 2022/0331465 A1* | 10/2022 | Childress | ................... | A61L 2/10 |
| 2023/0060451 A1* | 3/2023 | Cho | ......................... | B62B 3/04 |
| 2023/0117322 A1* | 4/2023 | Venturi | ................... | B62B 3/001 |
| | | | | 280/210 |
| 2024/0002174 A1* | 1/2024 | Martin | ................... | B65G 67/02 |

* cited by examiner

FOLDING CART FOR LOADING IN VEHICLE

CROSS REFERENCE TO RELATED APPLICATION

The present application claims priority of Korean Patent Application No. 10-2021-0113464 filed on Aug. 26, 2021, the entire contents of which is incorporated herein for all purposes by this reference.

TECHNICAL FIELD

The present invention relates to a folding cart for loading in a vehicle, which can simply operate a cart with luggage to be loaded in a luggage room or a trunk of the vehicle.

BACKGROUND

In general, when shopping at a large store or a shopping mall, a cart (shopping cart) is used to load and move purchased goods.

After purchasing the goods, the user moves the cart with the purchased goods to a vehicle, and then takes the goods out of the cart to load it into a storage space in the vehicle, or puts the goods in the cart into the shopping basket and then moves and loads the shopping basket to and in the storage space in the vehicle.

However, for seniors and the elderly who lack strength, it is difficult and inconvenient to take out the goods in the cart one by one and move and load them to the vehicle, and in severe cases, there is a risk of injury due to negligence.

The foregoing explained as the background is intended merely to aid in the understanding of the background of the present invention, and is not intended to mean that the present invention falls within the purview of the related art that is already known to those skilled in the art.

SUMMARY OF THE INVENTION

In preferred aspects, provided is a folding cart for loading in a vehicle, which can load a cart body with goods (luggage) in a luggage room or a trunk of a vehicle by a simple operation, and prevent breakage or damage to the goods by restricting the movement of the cart body loaded in the vehicle. As such, a user may load the purchased goods to the vehicle more easily.

In an aspect, provided is a folding cart for loading in a vehicle including a cart body configured to put and load goods; and a leg connected to the cart body and having a rotating wheel coupled thereto, in which the leg is formed in a three-section structure capable of height adjustment by a sliding structure and folding and unfolding operations by a rotation structure.

The folding cart for loading in the vehicle further includes a handle rotatably coupled to the cart body, in which the handle has a function of disinfecting the goods in the cart body.

The leg includes an upper leg vertically sliding and moving with respect to the cart body; an intermediate leg connected to the upper leg in the rotation structure; and a lower leg connected to the intermediate leg in the rotation structure, and a connection portion of the intermediate leg and the lower leg and the end of the lower leg are rotatably coupled to wheels, respectively.

The upper leg, the intermediate leg, and the lower leg are symmetrically provided on the left and right of the cart body and connected through a plurality of connection bars.

The cart body is provided with a guide frame vertically extending, and an upper end of the upper leg is inserted into the guide frame and coupled to be vertically movable along the guide frame.

The guide frame is formed with a guide hole vertically extending, upper and lower ends of the guide hole extend forward or backward, a leg pin supported by a spring is installed on the upper end of the upper leg to be movable forward or backward, the leg pin is connected to a lower end of a metal band, an upper end of the metal band is wound around a winding roller receiving a rotation force by the spring, and the winding roller is rotatably coupled to the guide frame above the guide hole.

All of a forward angle between the upper leg and the intermediate leg and a forward angle between a forward angle between the intermediate leg and the lower leg become obtuse angles, when the upper leg, the intermediate leg, and the lower leg are all unfolded and the cart maintains the standing state, and the upper leg and the intermediate leg, and the intermediate leg and the lower leg are supported by contact structures by projections, respectively to prevent a forward rotation of the upper leg and a backward rotation of the intermediate leg by the weight of the cart body in the standing state.

A lower end disc part of the upper leg and an upper end disc part of the intermediate leg face each other, the lower end disc part of the upper leg is provided with an inner projection, the upper end disc part of the intermediate leg is provided with an inner projection and an outer projection, and the inner projection of the lower end disc part of the upper leg and the inner projection of the upper end disc part of the intermediate leg contact each other when the cart is in the standing state, and the outer projection of the upper end disc part of the intermediate leg contacts the upper leg, thereby preventing the forward rotation of the upper leg by the weight of the cart body.

A lower end disc part of the intermediate leg and a rear disc part of the lower leg face each other, the lower end disc part of the intermediate leg is provided with an inner projection, a lower end disc part of the lower leg is provided with an inner projection and an outer projection, and the inner projection of the lower end disc part of the intermediate leg and the rear disc part of the lower leg contact each other when the cart is in the standing state, and the outer projection of the rear disc part of the lower leg contacts the intermediate leg, thereby preventing the backward rotation of the intermediate leg by the weight of the cart body.

When the cart body is loaded in a luggage room or a trunk of the vehicle, the upper leg is raised to be inserted into the guide frame, the intermediate leg is rotated backward and upward and folded with respect to the upper leg, and the lower leg is rotated backward and downward and folded with respect to the intermediate leg.

The cart body is provided with a cart rod whose length is changed to the side, and when the cart body is loaded in a luggage room or a trunk of a vehicle, the cart rod is changed in length to protrude to the side of the cart body, and both ends of the cart rod are supported in contact with a vehicle body, thereby restricting the movement of the cart body.

Both ends of the cart rod have a cart roller, which guides the movement of the cart body, rotatably coupled thereto.

Both ends of the handle are inserted into a handle groove provided on the cart body and rotatably coupled, and to control or restrict a rotation angle of the handle, the end of the handle is formed with a rotation projection and a stopper, and the handle groove is formed with a projection groove into which the rotation projection is inserted and a stopper groove into which the stopper is inserted.

The handle is provided with an ultra violet light emitting diode (UV LED) that performs disinfecting and sterilizing by radiating ultraviolet light. When the handle rotates to be folded to the cart body, the UV LED is exposed into the cart body through a body hole formed in the cart body.

The end of the handle and the cart body are provided with a contact switch and a contact projection configured to turn on or off an operation of the UV LED. When the handle rotates to be folded to the cart body, the UV LED is turned on by contacting the contact switch and the contact projection.

The folding cart for loading according to various exemplary embodiments may have a configuration that includes a cart body configured to load the goods, the leg capable of height adjustment and the folding and unfolding operations by the rotation, and the handle with sterilizing and disinfecting functions of the goods in the cart body. As such, the cart body with the goods (luggage) may be loaded in the luggage room or the trunk of the vehicle by the user's simple operation, thereby further facilitating the loading work of the purchased goods in the vehicle and the movement of the cart body loaded in the vehicle may be controlled, thereby preventing breakage or damage to the goods. Further, the UV LED may be provided on the handle in the state where the cart body is loaded in the vehicle to sterilize and disinfect the goods in the cart body, thereby performing the hygiene management of the cart more effectively.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION

Figure 1:
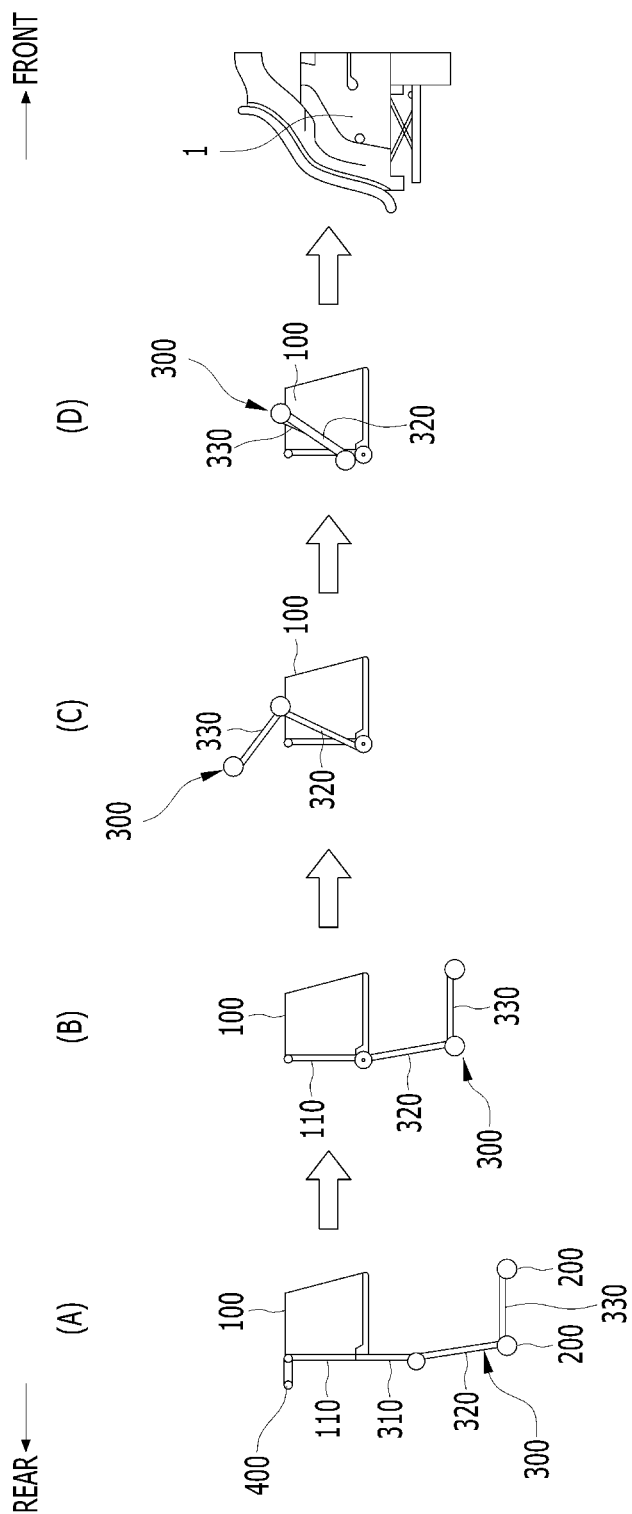
FIG. 1 shows a process of loading an exemplary folding cart for loading in a vehicle according to an exemplary embodiments of the present invention in a luggage room of the vehicle.

Specific structural to functional descriptions of the exemplary embodiments of the present invention disclosed in the present specification or application are only illustrated for the purpose of describing the exemplary embodiments according to the present invention, and the exemplary embodiments according to the present invention may be embodied in various forms and it should not be construed that the present invention is limited to the exemplary embodiments described in the present specification or application.

Since the embodiments according to the present invention may be variously changed and have various forms, specific exemplary embodiments will be illustrated in the drawings and described in detail in the present specification or application. However, this is not intended to limit the exemplary embodiments according to the concept of the present invention to a particular disclosed form, and it should be understood that the present invention includes all changes, equivalents, and substitutes included in the spirit and scope of the present invention.

Terms such as first and/or second may be used to describe various components, but the components should not be limited by the terms. The terms are used only for the purpose of distinguishing one component from another, and for example, without departing from the scope according to the concept of the present invention, the first component may be named a second component, and similarly, the second component may also be named the first component.

When a component is referred to as being "connected" or "coupled" to another component, the component may be directly connected or coupled to another component, but it should be understood that other components may also be present between the components. On the other hand, when a component is referred to as being "directly connected" or "directly coupled" to another component, it should be understood that there are no other components between the components. Other expressions which describe the relationship between the components, that is, "between" and "immediately between" or "neighboring" and "directly neighboring to" should be interpreted in the same manner.

The terminology used in the present specification is merely for the purpose of describing particular exemplary embodiments, and is not intended to limit the present invention. The singular forms may include plural forms unless the contexts clearly indicate the opposite. In the present specification, it may be understood that the term "comprising", "having", or the like specifies the presence of the characteristic, integer, step, operation, component, part, or a combination thereof described, and does not exclude the presence or addition possibility of one or more other characteristics, integers, steps, operations, components, parts, or combinations thereof in advance.

Unless defined otherwise, all terms including technical terms or scientific terms used herein have the same meaning as commonly understood by those skilled in the art to which the present invention pertains. The terms defined in the dictionary commonly used may be interpreted as having a meaning consistent with the meaning in the context of the related technology, and may not be interpreted as an ideal or excessively formal meaning, unless clearly defined in the present specification.

A control unit (controller) according to an exemplary embodiment of the present invention can be implemented through a non-volatile memory (not shown) configured to store data relating to an algorithm configured to control the operation of various components of a vehicle or software instructions for reproducing the algorithm and a processor (not shown) configured to perform operations described below using data stored in the corresponding memory. The memory and the processor may be implemented as separate chips. Alternatively, the memory and the processor may be implemented as a single chip integrated with each other. The processor can take the form of one or more processors.

Hereinafter, a folding cart for loading in a vehicle according to a preferred exemplary embodiment of the present invention will be described with reference to the accompanying drawings.

As shown in FIGS. 1 to 17, a folding cart for loading of a vehicle includes a cart body 100 configured to put and load goods, and a leg 300 connected to the cart body 100 and having a rotary wheel 200 coupled thereto, in which the leg 300 is formed in a three-section structure capable of height adjustment by a sliding structure and folding and unfolding operations by a rotation structure.

Further, the folding cart may further include a handle 400 rotatably coupled to the cart body 100, and the handle 400 may have a function of sterilizing the goods in the cart body 100.

The three-section leg 300 includes an upper leg 310 vertically sliding and moving with respect to the cart body 100, an intermediate leg 320 connected to the upper leg 310 in the rotation structure, and a lower leg 330 connected to the intermediate leg 320 in the rotation structure.

The connection portion of the intermediate leg 320 and the lower leg 330 and the end of the lower leg 330 are rotatably coupled to wheels 200 contacting the road surface, respectively.

The upper leg 310, the intermediate leg 320, and the lower leg 330 are symmetrically provided on the left and right of the cart body 100, and the left and right legs 300 have a structure of being connected through a plurality of connection bars 340.

When the leg 300 is symmetrically provided on the left and right of the cart body 100, the cart can be moved more stably, and the left and right legs 300 may be connected through the connection bar 340, thereby structurally reinforcing stiffness.

The connection bar 340 is coupled to connect the connection portion of the upper leg 310 and the intermediate leg 320, the connection portion of the intermediate leg 320 and the lower leg 330, and the end of the lower leg 330, respectively.

The connection bar 340 connecting the connection portion of the intermediate leg 320 and the lower leg 330, and the connection bar 340 connecting the end of the lower leg 330 may also serve as the rotation centers of the wheel 200, respectively.

The cart body 100 is provided with a guide frame 110 vertically extending, and an upper end of the upper leg 310 has a structure of being inserted into the guide frame 110 and coupled to be vertically movable along the guide frame 110.

As the upper leg 310 has the structure of vertically moving along the guide frame 110, the leg 300 has a structure capable of height adjustment by the sliding structure.

FIG. 1 shows a process in which the leg 300 is folded by the upward sliding movement and the rotation so that the folding cart according to an exemplary embodiment of the present invention is loaded in a luggage room (or trunk) of the vehicle in a standing state of being stood on the road surface.

Figure 2:
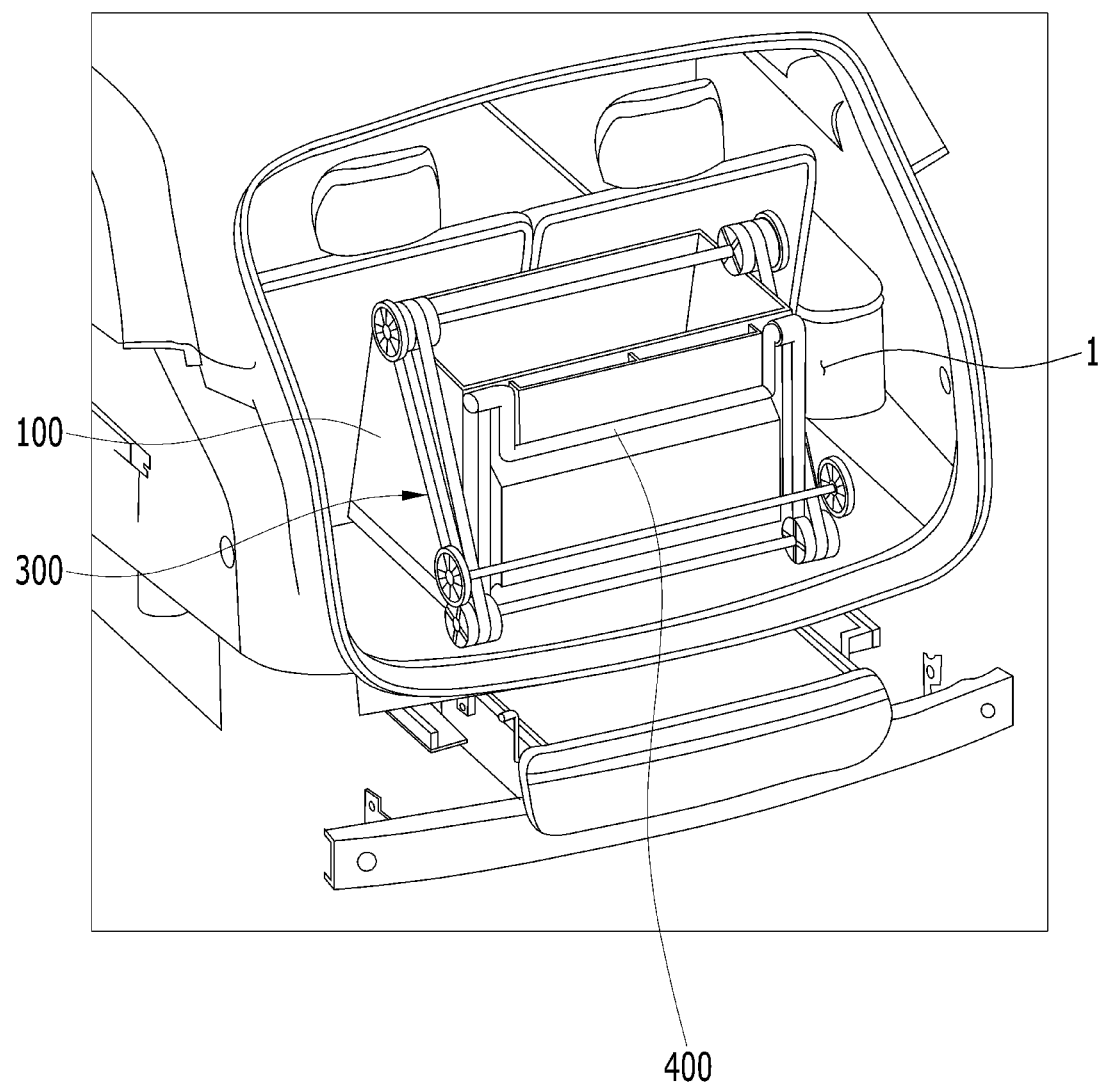
FIG. 2 shows a state where an exemplary cart body whose leg is folded is loaded in the luggage room of the vehicle according to an exemplary embodiments of the present invention.
Figure 3:
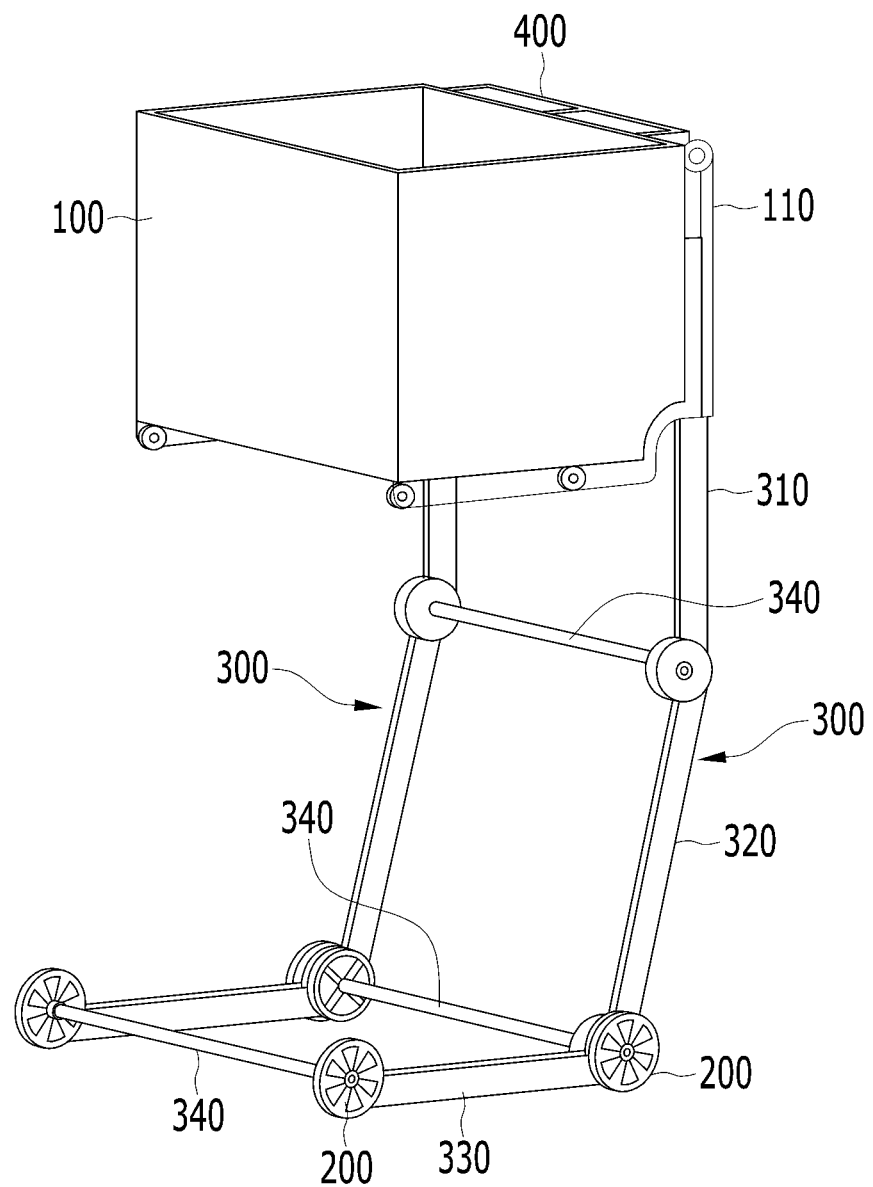
FIG. 3 shows a standing state of an exemplary folding cart for loading of the vehicle according to an exemplary embodiments of the present invention.
Figure 4:
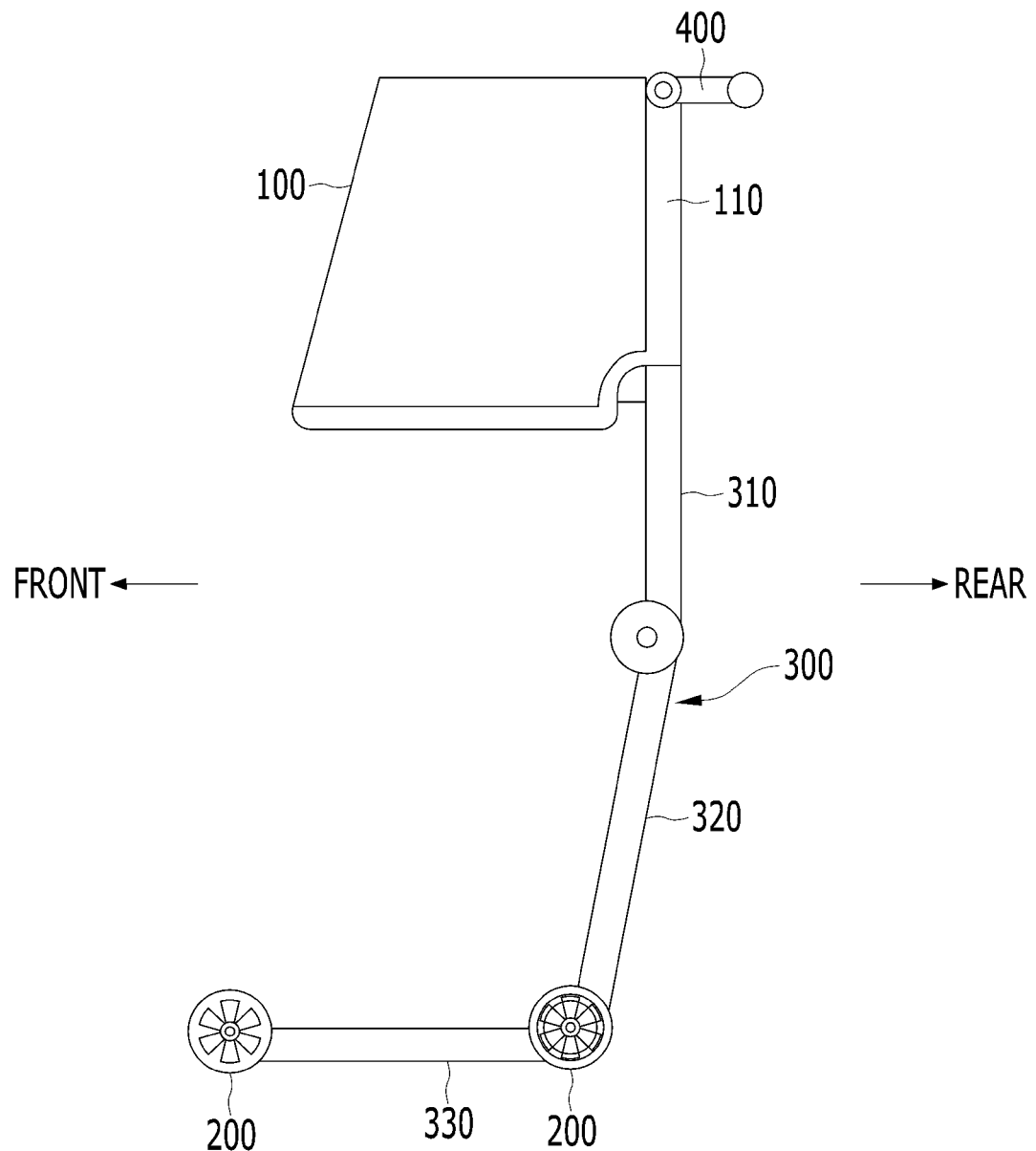
FIG. 4 shows a side diagram of FIG. 3.

In other words, in FIG. 1, a state (A) shows a situation in which the upper leg 310, the intermediate leg 320, and the lower leg 330 are all unfolded and the cart maintains the standing state, a state (B) shows a state where the upper leg 310 slides and moves upward to be inserted into the guide frame 110 in the state (A), a state (C) shows a state where the intermediate leg 320 is rotated backward and upward and folded in the state (B), and a state (D) shows a state where the lower leg 330 is rotated backward and downward and folded in the state (C), and in the state where the leg 300 is folded as in the state (D), the cart body 100 is loaded and stored in a luggage room 1 or a trunk of the vehicle, as shown in FIG. 2.

The guide frame 110 is formed with a guide hole 111 vertically extending, and upper and lower ends of the guide hole 111 are formed to extend forward or backward, and preferably, the upper and lower ends of the guide hole 111 are formed to extend backward after bent at right angles, respectively.

An upper end of the upper leg 310 is formed with a pin movement hole 311 extending forward or backward to penetrate left and right side surfaces of the upper leg 310, a leg pin 510 is installed to penetrate the pin movement hole 311, the leg pin 510 can move forward or backward along the pin movement hole 311, the leg pin 510 can be guided by the guide pin 520 to move forward or backward, and the guide pin 520 has one end fixed to the upper leg 310 and the other end connected to the leg pin 510, and is installed in a structure of being supported by a pin spring 530 of the leg pin 510.

The pin spring 530 is a coil spring and provides a spring force that pushes the leg pin 510 backward, and therefore, when an external force is not applied to the leg pin 510, the leg pin 510 maintains a state of being locked to a lower end or an upper end of the guide hole 111 by the spring force of the pin spring 530.

The upper end of the upper leg 310 is installed in a structure in which a portion including the leg pin 510 is inserted into the guide frame 110.

The leg pin 510 is connected to a lower end of a metal band 540, and an upper end of the metal band 540 is wound around a winding roller 560 receiving a rotation force by the spring force of a roller spring 550, and the winding roller 560 is installed in a structure of being rotatably coupled to the guide frame 110 above the guide hole 111.

The roller spring 550 is a spiral spring or a mainspring.

Figure 5:
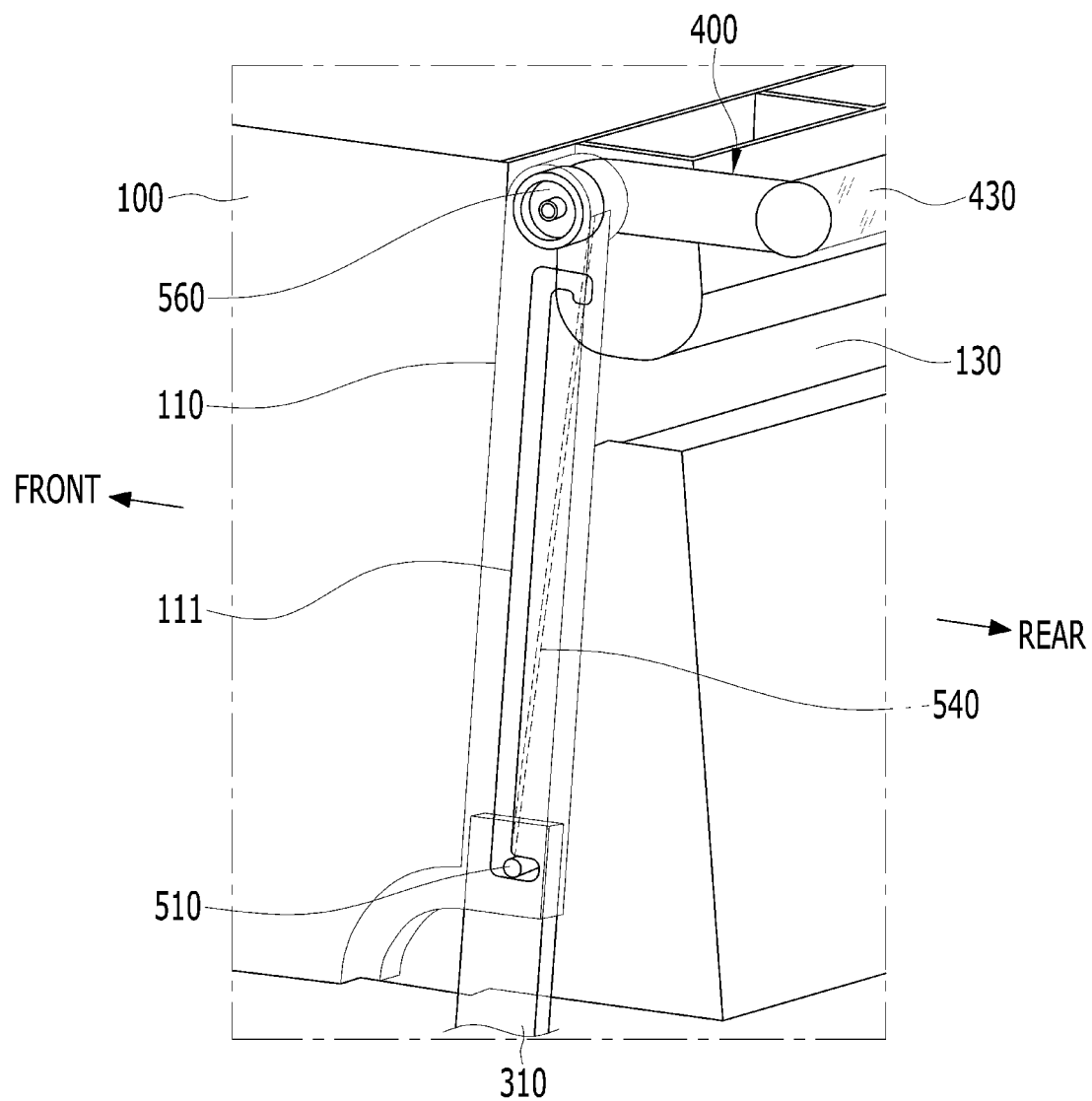
FIGS. 5 to 8 show diagrams for explaining an operation in which an upper leg is inserted into a guide frame according to an exemplary embodiments of the present invention.
Figure 6:
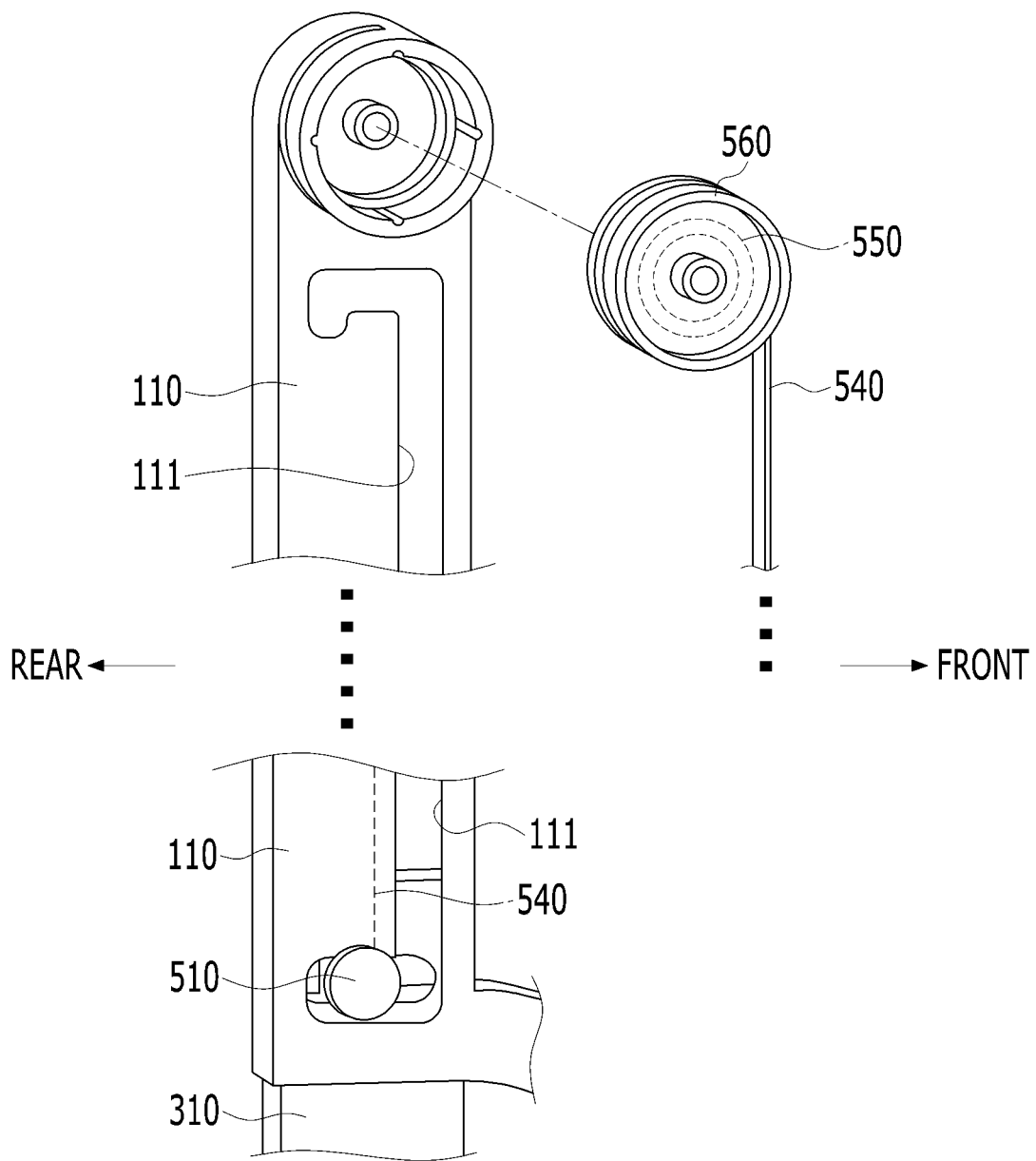
Figure 7:
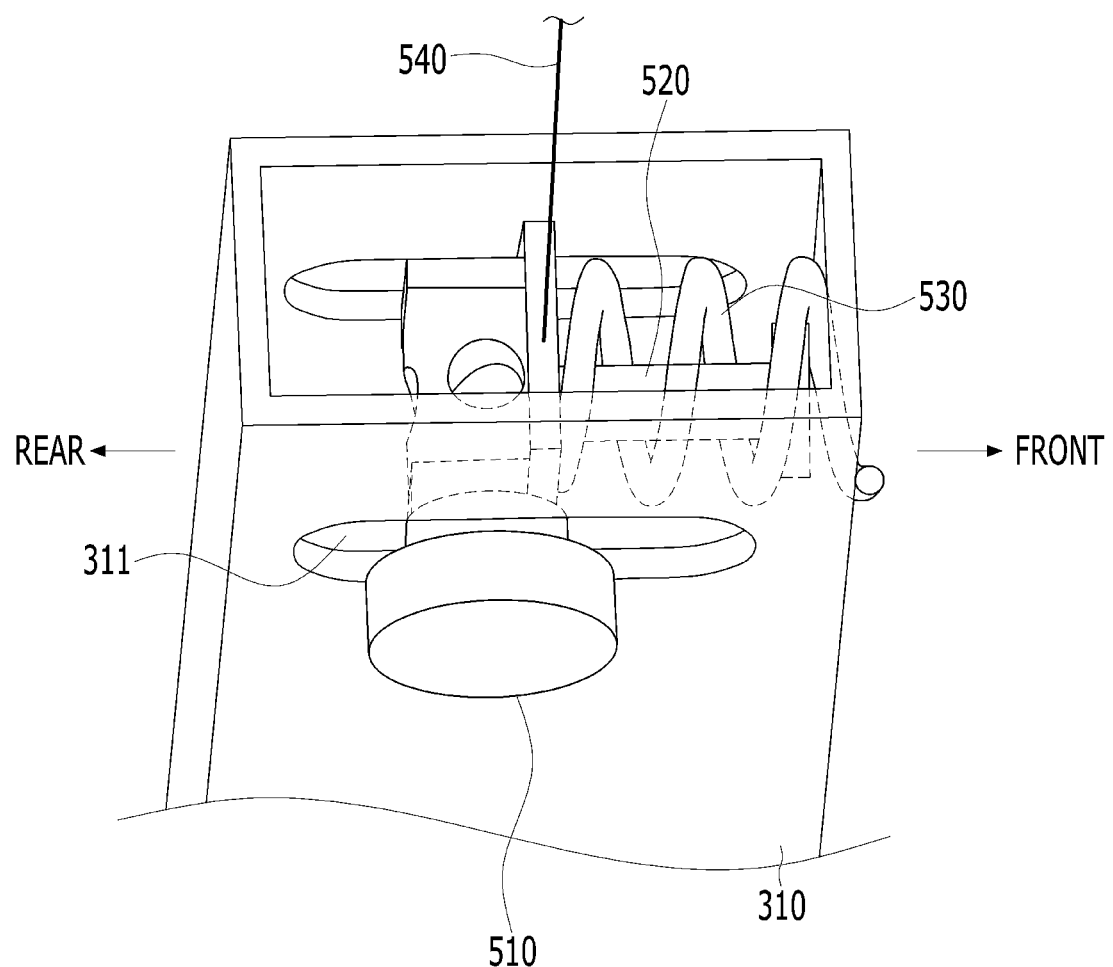

FIGS. 5 and 6 show a state where the upper leg 310 protrudes downward from the guide frame 110, and at this time, the leg pin 510 moves backward from the lower end of the guide hole 111 by the spring force of the pin spring 530 and is locked to the lower end of the guide hole 111, and the cart is in the standing state.

When the user operates and pushes the leg pin 310 forward to load the cart in the vehicle, the leg pin 310 is released from the state of being locked to the lower end of the guide hole 111, and at the same time, the winding roller 560 is rotated by the spring force of the roller spring 550, the metal band 540 is wound around the winding roller 560 by the rotation of the winding roller 560, and the metal band 540 pulls the leg pin 510 upward by the winding operation of the metal band 540.

Figure 8:
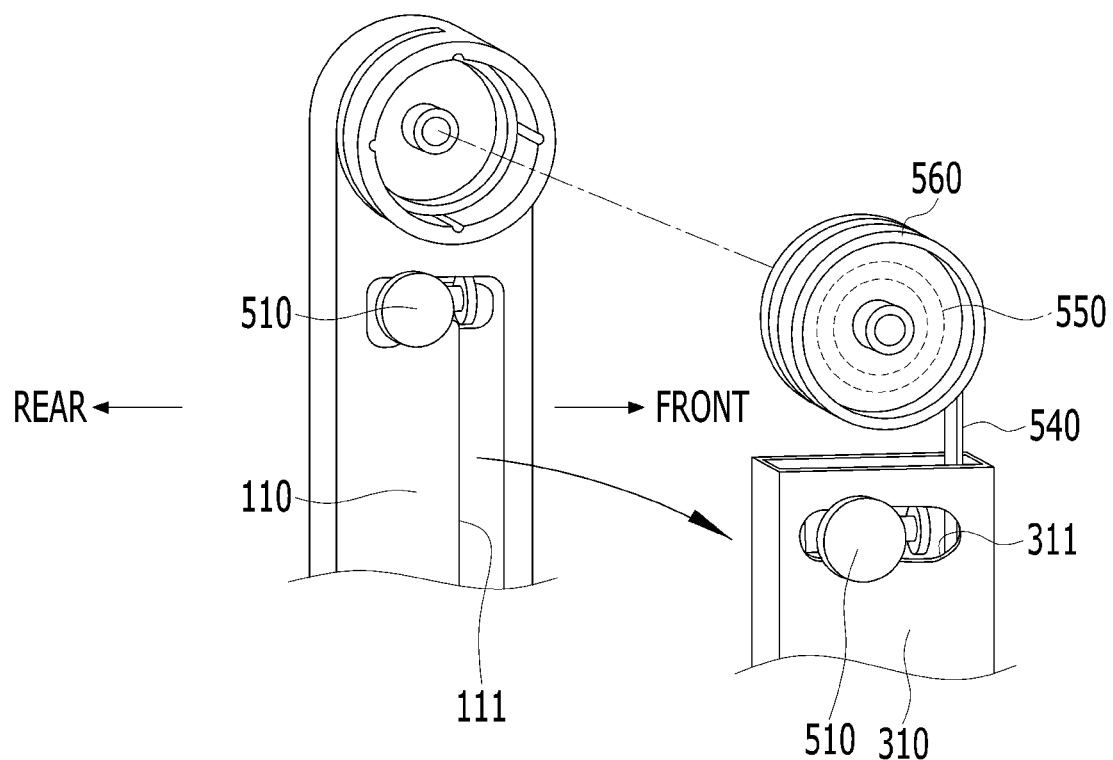

When the leg pin 510 moves upward along the guide hole 111 by the pulling force of the metal band 540, at this time, the upper leg 310 together with the leg pin 510 moves upward to be inserted into the guide frame 110, and finally, the leg pin 510 is in a state of being locked to the upper end of the guide hole 111, as shown in FIG. 8, and through such an operation, a height of the leg 300 is changed to a state of being reduced as shown in (B) of FIG. 1.

As described above, when the upper leg 310 is inserted into the guide frame 110 by the upward movement of the leg pin 510 and the height of the leg 300 is reduced, as described above with reference to FIG. 1, the cart body 100 is changed to a state of being folded by rotating the intermediate leg 320 backward and upward, and subsequently, changed to a state of being folded by rotating the lower leg 330 backward and downward, and then the cart body 100 in the state where the leg 300 is fully folded can be loaded and stored in the luggage room 1 or the trunk of the vehicle as shown in FIG. 2.

Figure 9:
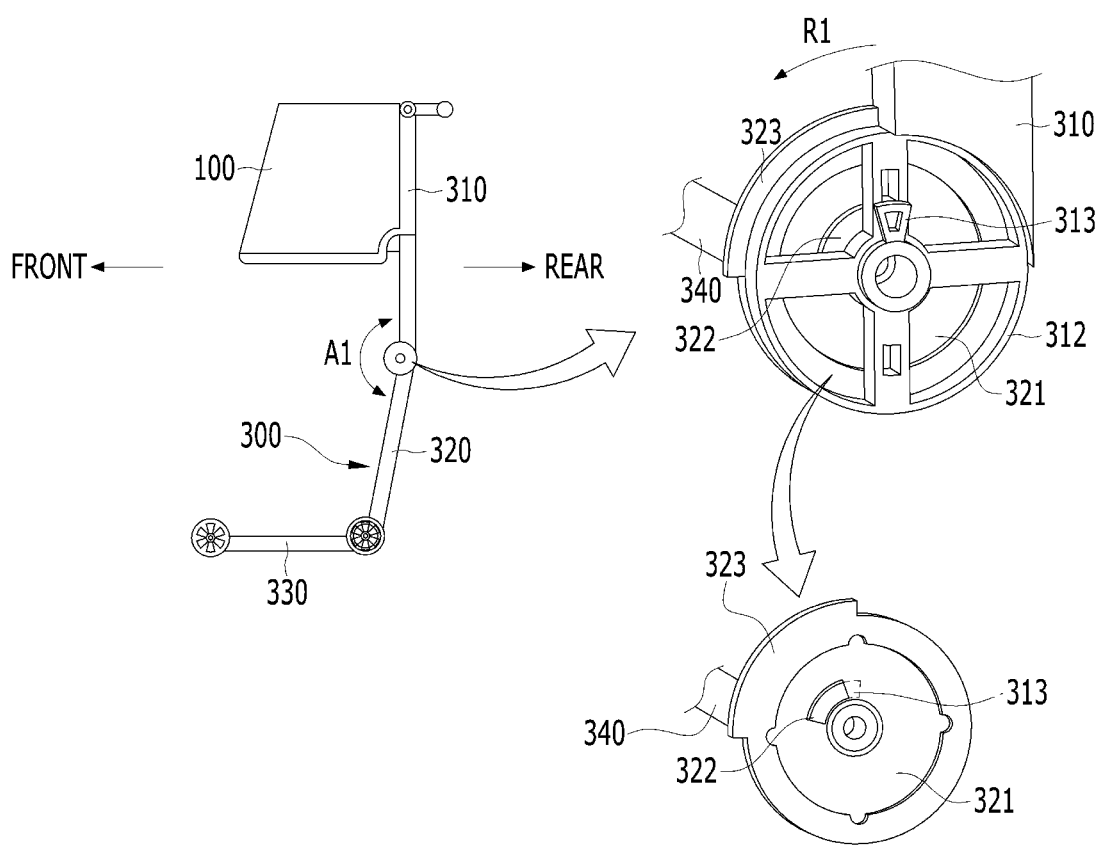
FIGS. 9 to 11 show diagrams for explaining a rotation restriction structure of the upper leg and an intermediate leg when the cart is in the standing state.
Figure 10:
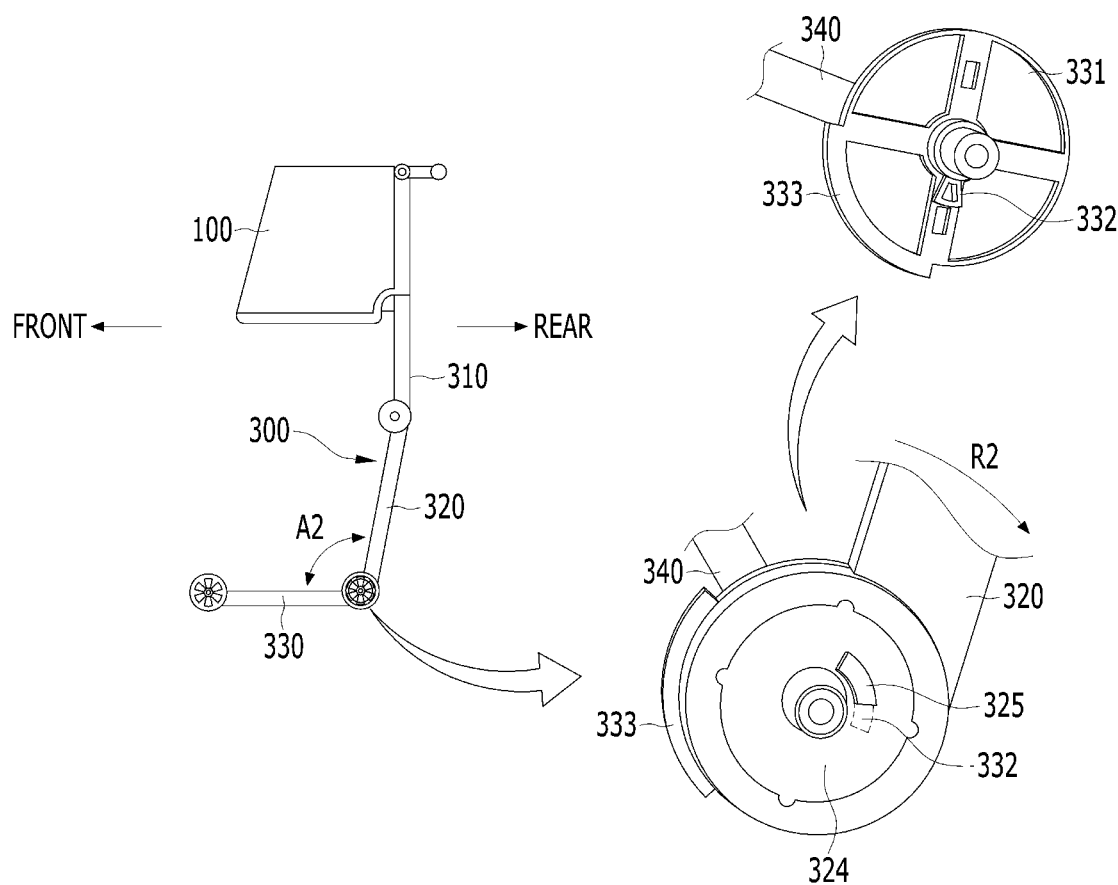

Meanwhile, as shown in FIGS. 9 and 10, according to an exemplary embodiment of the present invention, all of a forward angle (A1) between the upper leg 310 and the intermediate leg 320 and a forward angle (A2) between the intermediate leg 320 and the lower leg 330 maintain obtuse angles, when the upper leg 310, the intermediate leg 320, and the lower leg 330 are all unfolded and the cart maintains the standing state.

Therefore, the upper leg 310 and the intermediate leg 320, and the intermediate leg 320 and the lower leg 330 have structures of being supported by contact structures by projections, respectively, to prevent the forward rotation of the upper leg 310 and the backward rotation of the intermediate leg 320 by the weight of the cart body 100 when the cart is in the standing state.

In other words, as shown in FIG. 9, when the cart is in the standing state, a lower end disc part 312 of the upper leg 310 and an upper end disc part 321 of the intermediate leg 320 face each other, the lower end disc part 312 of the upper leg 310 is provided with an inner projection 313, and the upper end disc part 321 of the intermediate leg 320 is provided with an inner projection 322 and an outer projection 323.

Further, when the cart is in the standing state, the inner projection 313 of the lower end disc part 312 of the upper leg 310 and the inner projection 322 of the upper end disc part 321 of the intermediate leg 320 contact each other, and the outer projection 323 of the upper end disc part 321 of the intermediate leg 320 can contact the upper leg 310, thereby preventing the forward rotation (arrow R1) of the upper leg 310 by the weight of the cart body 100.

Particularly, the cart has a structure capable of preventing the forward rotation of the upper leg 310 by the weight of the cart body 100 through the double support structure of the inner projections 313, 322 and the outer projection 323 when the cart is in the standing state.

Figure 11:
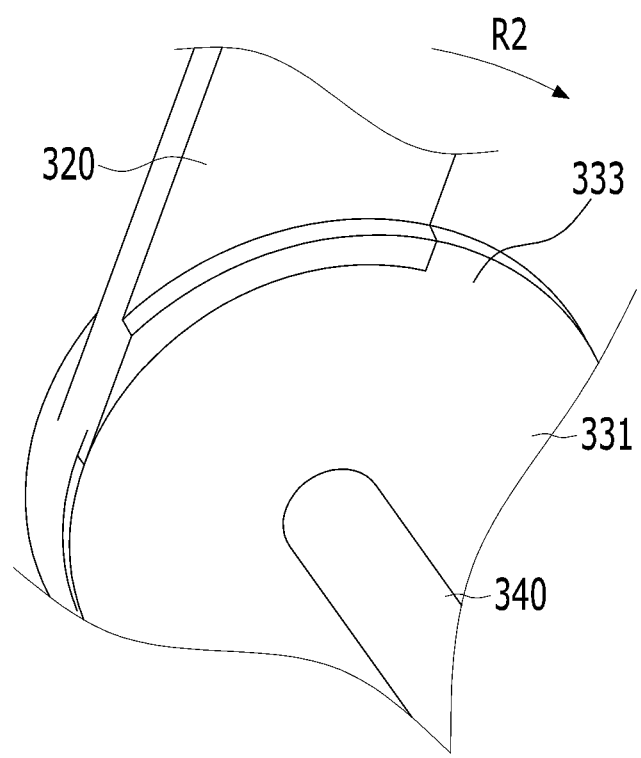

Further, as shown in FIGS. 10 and 11, when the cart is in the standing state, a lower end disc part 324 of the intermediate leg 320 and a rear disc part 331 of the lower leg 330 face each other, the lower end disc part 324 of the intermediate leg 320 is provided with an inner projection 325, and the rear disc part 331 of the lower leg 330 is provided with an inner projection 332 and an outer projection 333.

Further, when the cart is in the standing state, the inner projection 325 of the lower end disc part 324 of the intermediate leg 320 and the inner projection 332 of the rear disc part 331 of the lower leg 330 contact each other, and the outer projection 333 of the rear disc part 331 of the lower leg 330 can contact the intermediate leg 320, thereby preventing the backward rotation (arrow R2) of the intermediate leg 320 by the weight of the cart body 100.

Particularly, the cart has the structure capable of preventing the backward rotation of the intermediate leg 320 by the weight of the cart body 100 through the double support structure of the inner projections 325, 332 and the outer projection 333 when the cart is in the standing state.

Figure 12:
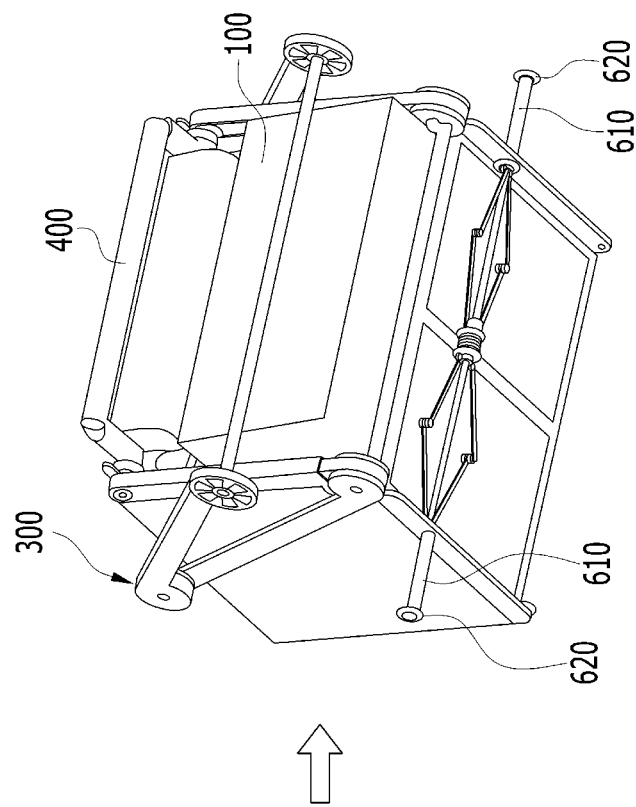
FIGS. 12 and 13 show diagrams for explaining a cart rod according to an exemplary embodiments of the present invention.
Figure 12:
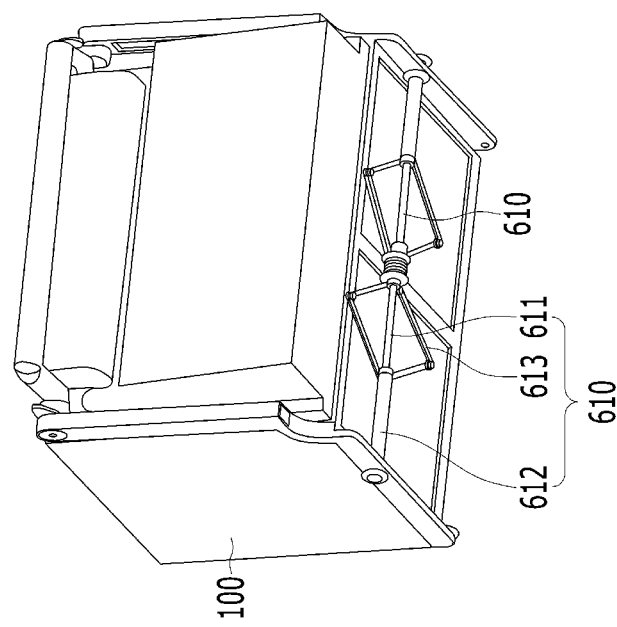
Figure 13:
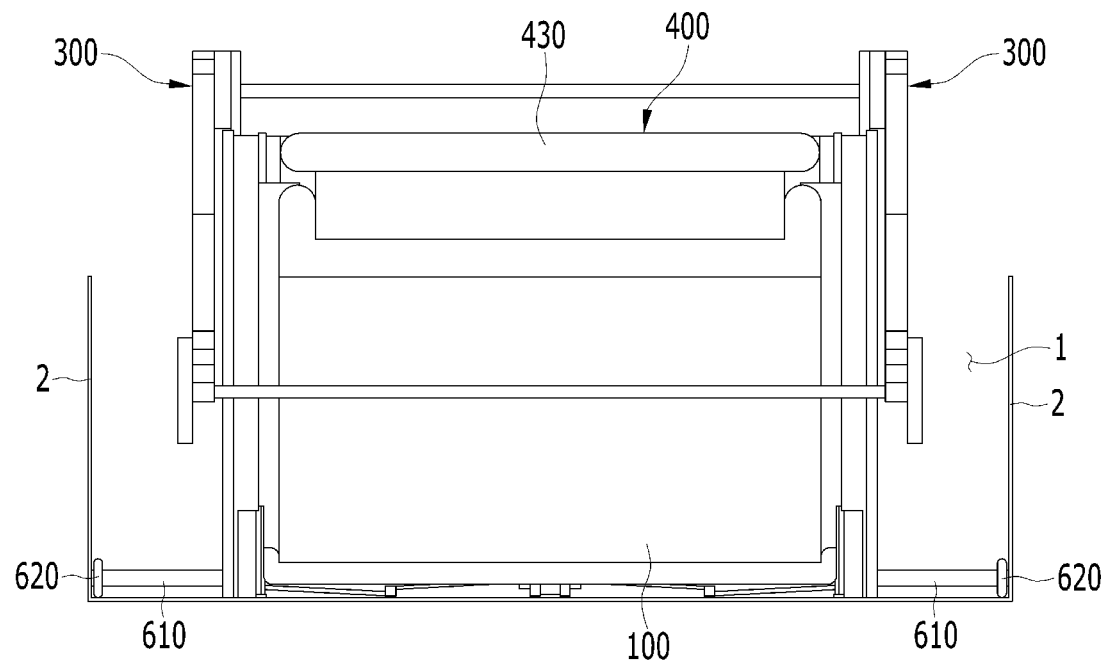
Figure 14:
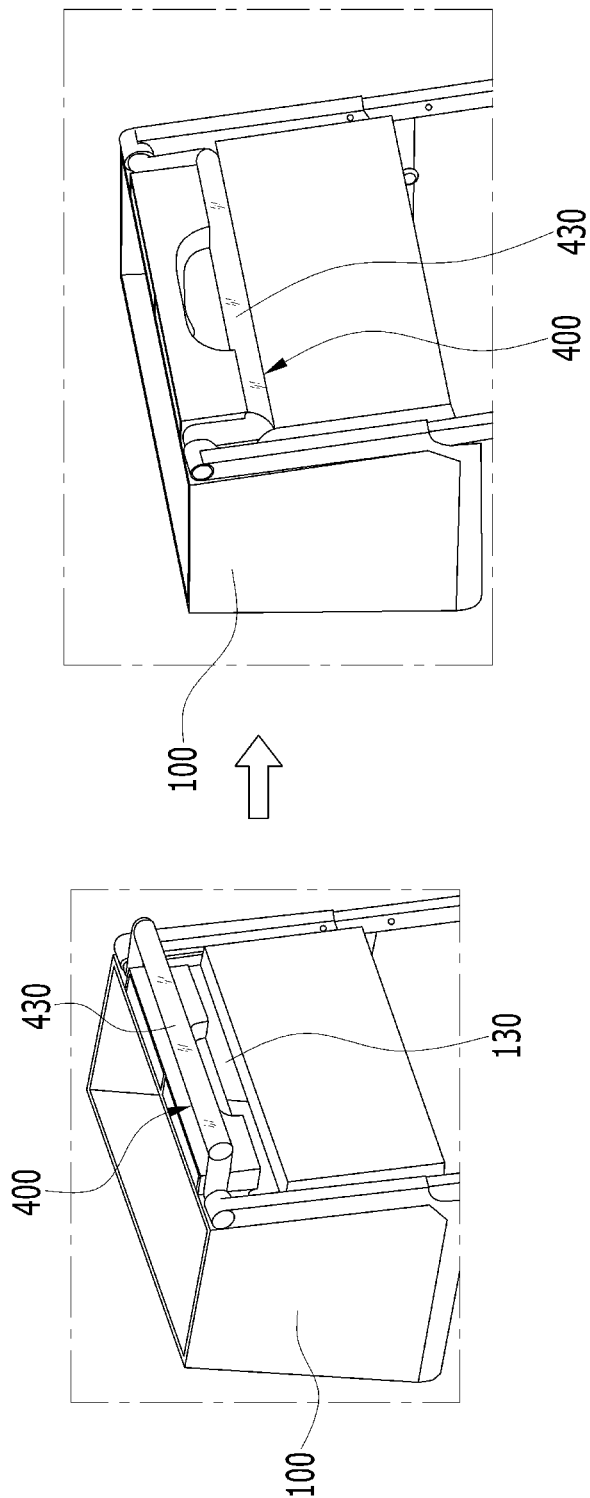
FIGS. 14 to 17 show diagrams for explaining a handle provided with a UV LED according to an exemplary embodiments of the present invention.
Figure 15:
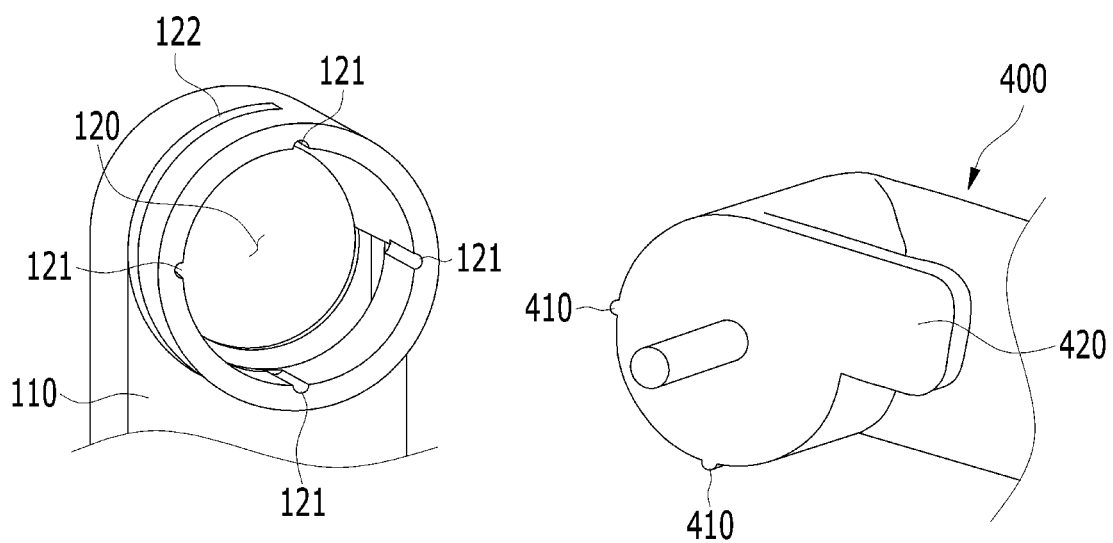
Figure 16:
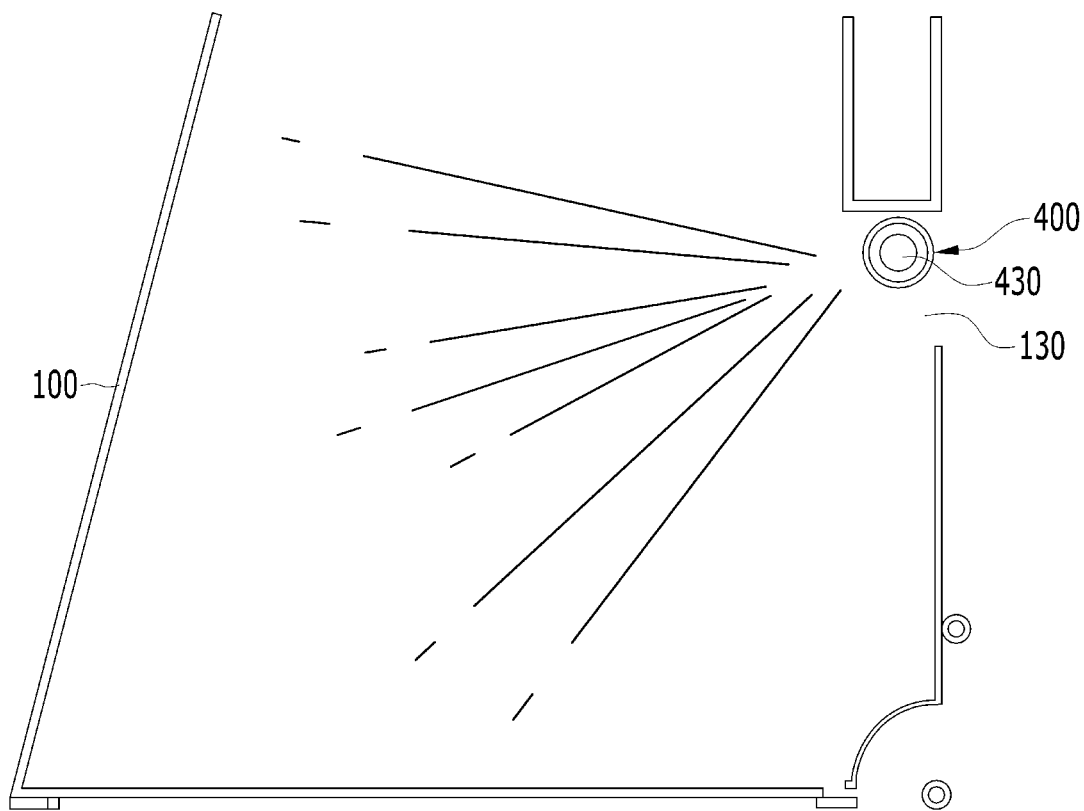
Figure 17:
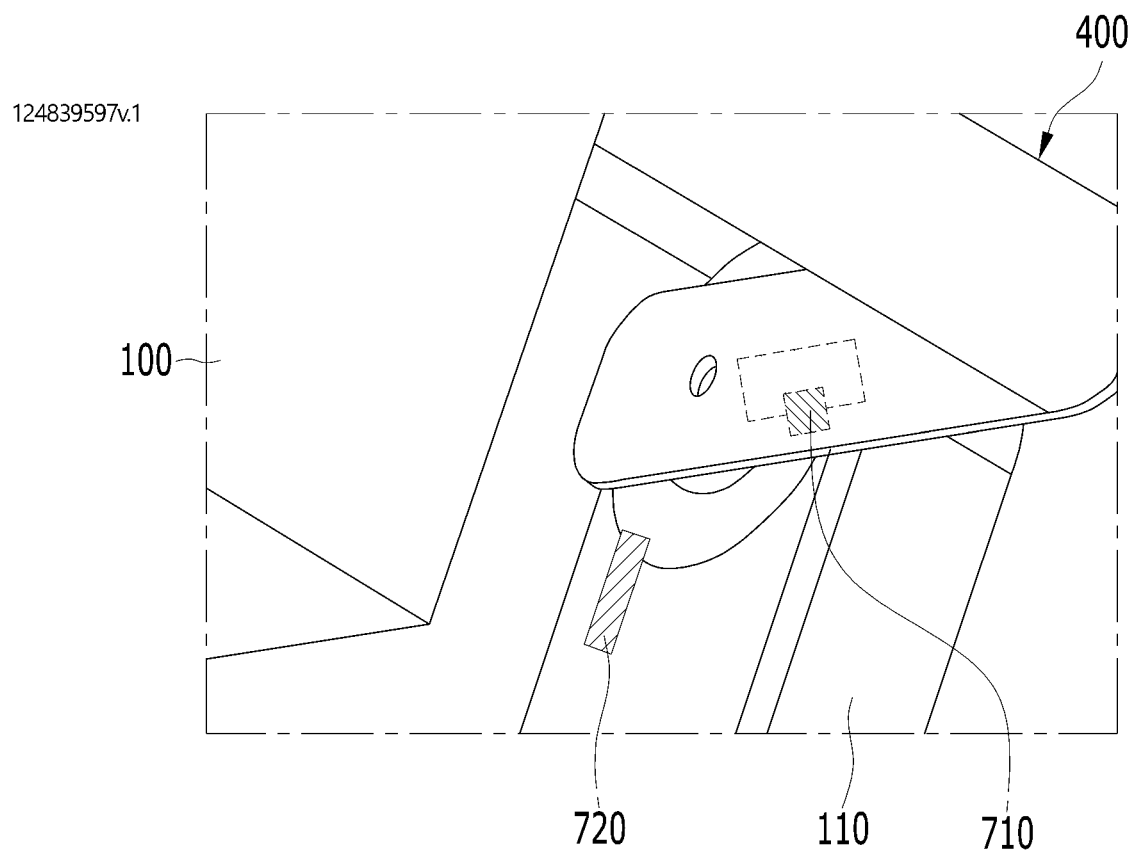

As shown in FIGS. 12 and 13, the cart body 100 is provided with a cart rod 610, and when the cart body 100 is in the state of being loaded in the luggage room 1 or the trunk of the vehicle, the cart rod 610 is changed in length to protrude to the side of the cart body 100, and both ends of the cart rod 610 can be supported in contact with a vehicle body 2, thereby controlling or restricting the movement of the cart body 100.

The cart rod 610 is provided on an outer bottom of the cart body 100, and the cart rod 610 protrudes to the side of the cart body 100 when the length thereof is changed to increase.

The vehicle body 2 contacting both ends of the cart rod 610 becomes a side panel of the luggage room 1 or the trunk.

There is an advantage in that it is possible to prevent breakage or damage to the goods in the cart body 100 as much as possible, when the movement of the cart body 100 loaded and stored in the luggage room 1 or the trunk of the vehicle is restricted by the cart rod 610.

The cart rod 610 includes a bolt part 611 such as a lead screw fixed and coupled to an outer bottom of the cart body 100, a nut part 612 moving along the bolt part 611 upon rotation, and a rod part 613 connecting the bolt part 611 and the nut part 612.

The cart rod 610 including the bolt part 611, the nut part 612, and the rod part 613 can be a pantograph jack using the expansion and contraction of a rhombic frame.

Both ends of the cart rod 610 are rotatably coupled to a cart roller 620 to help the movement of the cart body 100 when the cart body 100 is loaded in the luggage room 1 or the trunk of the vehicle, and the cart roller 620 rotates in contact with the bottom of the luggage room 1 or the trunk.

Further, according to an exemplary embodiment of the present invention, as shown in FIGS. 14 to 17, both ends of the handle 400 are inserted into a handle groove 120 provided in the cart body 100 to be rotatably coupled, and to restrict a rotation angle of the handle 400, the end of the handle 400 is formed with a rotation projection 410 and a stopper 420, and the handle groove 120 is formed with a projection groove 121 into which the rotation projection is inserted, and a stopper groove 122 into which the stopper 420 is inserted.

The handle groove 120 may be provided on the upper end of the guide frame 110 provided on the cart body 100.

The projection groove 121 is formed on multiple portions spaced apart from each other at regular intervals along an inner circumferential surface of the handle groove 120, the stopper groove 122 penetrating the handle groove 120 in a radius direction and extending in the circumference direction is formed, the end of the handle 400 is formed with the rotation projection 410 on the portion spaced in the circumference direction, and the stopper 420 is formed to protrude outward from the end of the handle 400.

Therefore, the rotation angle of the handle 400 is determined by coupling the rotation projection 410 and the protrusion groove 121 upon rotation of the handle 400, and in particular, the maximum rotation angle of the handle 400 is determined at the moment when the stopper 420 contacts the end of the stopper groove 122.

Moreover, the handle 400 is provided with an ultraviolet light emitting diode (UV LED) 430 configured to disinfect and sterilize by radiation of ultraviolet light. For example, when the handle 400 rotates to be folded to the cart body 100, the UV LED 430 has a structure of being exposed into the cart body 100 through a body hole 130 formed in the cart body 100.

The ultraviolet light generated by the UV LED 430 may be radiated into the cart body 100 through the body hole 130 to sterilize and disinfect the goods loaded in the cart body 100.

The cart has a structure in which the end of the handle 400 and the cart body 100 are provided with a contact switch 710 and a contact projection 720 configured to turn on or off an operation of the UV LED 430, and the UV LED 430 is turned on by contacting the contact switch 710 and the contact projection 720 when the handle 400 rotates to be folded to the cart body 100.

The contact projection 720 may be provided on the upper end of the guide frame 110 provided on the cart body 100.

As described above, the folding cart for loading in the vehicle according to various exemplary embodiments of the present invention has a configuration that includes a cart body 100 configured to load the goods, the leg 300 capable of height adjustment and the folding and unfolding operations by the rotation, and the handle 400 with sterilizing and disinfecting functions of the goods in the cart body 100. As such, a user can load the cart body with the goods (luggage) in the luggage room 1 or the trunk of the vehicle with simple operation, thereby further facilitating the loading work of the purchased goods in the vehicle, to control the movement of the cart body 100 loaded in the vehicle, thereby preventing breakage or damage to the goods. In addition, the UV LED 430 may be provided on the handle 400 in the state where the cart body 100 is loaded in the vehicle to sterilize and disinfect the goods in the cart body 100 thereby performing the hygiene management of the cart more effectively.

While the present invention has been shown and described with reference to preferred exemplary embodiments, it will be apparent to those skilled in the art that the present invention can be variously improved and modified without departing from the technical spirit of the present invention provided by the appended claims.

What is claimed is:

1. A folding cart for loading in a vehicle comprising:
   a cart body configured to put and load goods;
   a leg connected to the cart body and having a rotating wheel coupled thereto; and
   a handle rotatably coupled to the cart body,
   wherein the leg is formed in a three-section structure capable of height adjustment by a sliding structure and folding and unfolding operations by a rotation structure, and
   wherein the handle has a function of disinfecting the goods in the cart body.

2. The folding cart for loading in the vehicle of claim 1, wherein both ends of the handle are inserted into a handle groove provided on the cart body and rotatably coupled, and
   wherein to control a rotation angle of the handle, the end of the handle is formed with a rotation projection and a stopper, and the handle groove is formed with a projection groove into which the rotation projection is inserted and a stopper groove into which the stopper is inserted.

3. The folding cart for loading in the vehicle of claim 1, wherein the handle is provided with an ultra violet light emitting diode (UV LED) that performs disinfecting and sterilizing by radiating ultraviolet light, and
   wherein when the handle rotates to be folded to the cart body, the UV LED is exposed into the cart body through a body hole formed in the cart body.

4. The folding cart for loading in the vehicle of claim 3, wherein the end of the handle and the cart body are provided with a contact switch and a contact projection configured to turn on or off an operation of the UV LED, and
   wherein when the handle rotates to be folded to the cart body, the UV LED is turned on by contacting the contact switch and the contact projection.

5. A folding cart for loading in a vehicle comprising:
   a cart body configured to put and load goods; and
   a leg connected to the cart body and having a rotating wheel coupled thereto,
   wherein the leg is formed in a three-section structure capable of height adjustment by a sliding structure and folding and unfolding operations by a rotation structure,
   wherein the leg comprises:
   an upper leg vertically sliding and moving with respect to the cart body;
   an intermediate leg connected to the upper leg in the rotation structure; and
   a lower leg connected to the intermediate leg in the rotation structure, and
   wherein the intermediate leg and the lower leg are rotatably coupled to wheels, respectively.

6. The folding cart for loading in the vehicle of claim 5, wherein the upper leg, the intermediate leg, and the lower leg are symmetrically provided on the left and right of the cart body and connected through a plurality of connection bars.

7. The folding cart for loading in the vehicle of claim 5, wherein the cart body is provided with a guide frame vertically extending, and
   wherein an upper end of the upper leg is inserted into the guide frame and coupled to be vertically movable along the guide frame.

8. The folding cart for loading in the vehicle of claim 7, wherein the guide frame is formed with a guide hole vertically extending,
   wherein upper and lower ends of the guide hole extend forward or backward,
   wherein a leg pin supported by a spring is installed on the upper end of the upper leg to be movable forward or backward,
   wherein the leg pin is connected to a lower end of a metal band,
   wherein an upper end of the metal band is wound around a winding roller receiving a rotation force by the spring, and
   wherein the winding roller is rotatably coupled to the guide frame above the guide hole.

9. The folding cart for loading in the vehicle of claim 5, wherein all of a forward angle between the upper leg and the intermediate leg and a forward angle between a forward angle between the intermediate leg and the lower leg become obtuse angles, when the upper leg, the intermediate leg, and the lower leg are all unfolded and the cart maintains the standing state, and
   wherein the upper leg and the intermediate leg, and the intermediate leg and the lower leg are supported by contact structures by projections, respectively to prevent a forward rotation of the upper leg and a backward rotation of the intermediate leg by the weight of the cart body in the standing state.

10. The folding cart for loading in the vehicle of claim 9, wherein a lower end disc part of the upper leg and an upper end disc part of the intermediate leg face each other,
    wherein the lower end disc part of the upper leg is provided with an inner projection,
    wherein the upper end disc part of the intermediate leg is provided with an inner projection and an outer projection, and wherein the inner projection of the lower end disc part of the upper leg and the inner projection of the upper end disc part of the intermediate leg contact each other when the cart is in the standing state, and the outer projection of the upper end disc part of the intermediate leg contacts the upper leg, thereby preventing the forward rotation of the upper leg by the weight of the cart body.

11. The folding cart for loading in the vehicle of claim 9, wherein a lower end disc part of the intermediate leg and a rear disc part of the lower leg face each other,
   wherein the lower end disc part of the intermediate leg is provided with an inner projection,
   wherein a lower end disc part of the lower leg is provided with an inner projection and an outer projection, and
   wherein the inner projection of the lower end disc part of the intermediate leg and the rear disc part of the lower leg contact each other when the cart is in the standing state, and the outer projection of the rear disc part of the lower leg contacts the intermediate leg, thereby preventing the backward rotation of the intermediate leg by the weight of the cart body.

12. The folding cart for loading in the vehicle of claim 7, wherein when the cart body is loaded in a luggage room or a trunk of the vehicle, the upper leg is raised to be inserted into the guide frame,
   the intermediate leg is rotated backward and upward and folded with respect to the upper leg, and
   the lower leg is rotated backward and downward and folded with respect to the intermediate leg.

13. A folding cart for loading in a vehicle comprising:
   a cart body configured to put and load goods; and
   a leg connected to the cart body and having a rotating wheel coupled thereto,
   wherein the leg is formed in a three-section structure capable of height adjustment by a sliding structure and folding and unfolding operations by a rotation structure,
   wherein the cart body is provided with a cart rod whose length is changed to the side,
   wherein when the cart body is loaded in a vehicle, the cart rod is changed in length to protrude to the side of the cart body, and
   wherein ends of the cart rod are supported in contact with a vehicle body, thereby restricting the movement of the cart body.

14. The folding cart for loading in the vehicle of claim 13, wherein both ends of the cart rod have a cart roller, which guides the movement of the cart body, rotatably coupled thereto.

* * * * *